United States Patent
Kawashima et al.

(10) Patent No.: US 6,251,900 B1
(45) Date of Patent: Jun. 26, 2001

(54) HETEROCYCLIC COMPOUNDS AND ANTITUMOR AGENT CONTAINING THE SAME AS ACTIVE INGREDIENT

(75) Inventors: Seiichiro Kawashima; Toshiyuki Matsuno; Shinichi Yaguchi; Tetsuo Watanabe; Masahiro Inaba, all of Tokyo (JP)

(73) Assignee: Zenyaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/463,214

(22) PCT Filed: Jul. 24, 1998

(86) PCT No.: PCT/JP98/03308

§ 371 Date: Jan. 21, 2000

§ 102(e) Date: Jan. 21, 2000

(87) PCT Pub. No.: WO99/05138

PCT Pub. Date: Feb. 4, 1999

(30) Foreign Application Priority Data

Jul. 24, 1997 (JP) .................................................. 9-198804

(51) Int. Cl.[7] ........................ A61K 31/5377; A61P 35/00; C07D 413/14
(52) U.S. Cl. ........................ 514/231.5; 514/241; 514/273; 544/106; 544/198; 544/199; 544/209; 544/324; 544/325
(58) Field of Search ..................................... 544/106, 198, 544/199, 209, 324, 325; 514/231.5, 241, 273

(56) References Cited

FOREIGN PATENT DOCUMENTS 6-507643 * 9/1994 (JP) .
9-48776 * 2/1997 (JP) .

* cited by examiner

Primary Examiner—Richard L. Raymond
Assistant Examiner—Venkataraman Balasubramanian
(74) Attorney, Agent, or Firm—Oblon, Spivak, McClelland, Maier & Neustadt, P.C.

(57) ABSTRACT

Heterocyclic compounds in which s-triazine or pyrimidine is substituted with benzimidazole and morpholine and which are represented by the Formula I or phermaceutically acceptable acid addition salts thereof:

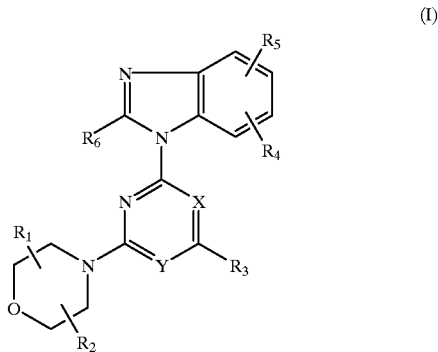

(I)

wherein X and Y respectively represent nitrogen atom or one of them represents nitrogen atom and the other represents C—$R_7$ wherein $R_7$ represents hydrogen or halogen atom; $R_1$, $R_2$, $R_4$, $R_5$ and $R_6$ represent hydrogen atom or $C_1$–$C_6$ alkyl; $R_3$ represents morpholino, piperidino, piperazinyl, thiomorpholino, benzimidazolyl, cyano or the like.

13 Claims, No Drawings

HETEROCYCLIC COMPOUNDS AND ANTITUMOR AGENT CONTAINING THE SAME AS ACTIVE INGREDIENT

TECHNICAL FIELD

The present invention relates to heterocyclic compounds in which s-triazine or pyrimidine is substituted with benzimidazole and morpholine and which are represented by the Appearanceula (I) or pharmaceutically acceptable acid addition salts thereof and antitumor agents containing the heterocyclic compounds as effective components:

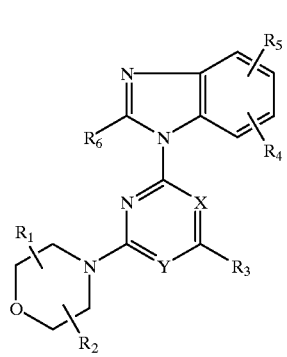

wherein X and Y respectively represent nitrogen atom or one of them represents nitrogen atom and the other represents C—$R_7$ wherein $R_7$ represents hydrogen or halogen atom; $R_1$, $R_2$, $R_4$, $R_5$ and $R_6$ represent hydrogen atom or $C_1$–$C_6$ alkyl; $R_3$ represents morpholino (which may be substituted with one or two $C_1$–$C_6$ alkyl, trifluoromethyl, hydroxymethyl, monohalogenomethyl or —$CH_2NR_8R_9$ wherein $R_8$ represents hydrogen atom or $C_1$–$C_6$ alkyl and Rg represents hydrogen atom, $C_1$–$C_6$ alkoxycarbonyl or benzyl), piperidino (which may be substituted with hydroxy, acetoxy, oxo, ethylenedioxy or amino $C_1$–$C_6$ alkyl), piperazinyl (which may be substituted with $C_1$–$C_6$ alkyl), thiomorpholino, benzimidazolyl, cyano or —$NR_{10}R_{11}$ wherein $R_{10}$ and $R_{11}$ represent hydrogen atom, $C_1$–$C_6$ alkyl, hydroxy $C_1$–$C_6$ alkyl or morpholino $C_1$–$C_6$ alkyl.

BACKGROUND ART s-Triazine (1,3,5-triazine) and pyrimidine derivatives have been researched in the fields of synthetic resins, synthetic fibers, dyes and agricultural chemicals and a number of such compounds have been synthesized. In the field of pharmaceuticals, researches have been made with respect to antitumor, anti-inflammatory, analgesic and antispasmodic activities. Especially, hexamethylmelamine (HMM) is well-known, which has been developed as analogue of antitumor agent triethylenemelamine (TEM) [B. L. Johnson et al. Cancer, 42: 2157–2161(1978)].

TEM is known as alkylating agent and is an s-triazine derivative having cytotoxic antitumor activity. HMM has been marketed in Europe under the indications for the treatment of ovarian and small cell lung cancers, and its action on solid cancers have attractive.

Among the s-triazine derivatives, imidazolyl-s-triazine derivatives are well-known which exhibit cytotoxic and selective aromatase inhibiting activities and have been proposed as medicine for estrogen-dependent diseases such as endometriosis, multicystic ovarium, mastosis, endometrium carcinoma and breast cancer (PCT publication WO93/17009).

However, there is still room for improvement on HMM with respect to its antitumor spectrum and intensity of antitumor activities against solid cancers. As to imidazolyl-s-triazine derivatives, they are limitative in application since they exhibit considerably higher aromatase inhibitory activities than their cytotoxic activities and application of them to cancerous patients other than those who suffer from estrogen-dependent diseases may lead to development of secondary effects such as menstrual disorders due to lack of estrogen. There are still, therefore, strong demands on medicines with no aromatase inhibitory activities and effective for solid cancers.

DISCLOSURE OF THE INVENTION

In order to expand antitumor spectrum of and increase antitumor activities of HMM, we, the inventors, carried out intensive studies on s-triazine and pyrimidine derivatives to surprisingly find out that heterocyclic compounds with substitution of benzimidazole and morpholine and represented by the Formula I exhibit by far strong antitumor activities with no aromatase inhibitory activities in comparison with the conventional s-triazine and pyrimidine derivatives, thus accomplishing the present invention.

The terms used for definition of letters in the Formula I, by which the heterocyclic compounds of the invention are represented, will be defined and exemplified in the following.

The term "$C_1$–$C_6$" refers to a group having 1 to 6 carbon atoms unless otherwise indicated.

The "$C_1$–$C_6$ alkyl group" refers to a straight- or branched-chain alkyl group such as methyl, ethyl, n-propyl, isopropyl, n-butyl, tert-butyl, n-pentyl or n-hexyl.

The "amino $C_1$–$C_6$ alkyl group" refers to the above-mentioned "$C_1$–$C_6$ alkyl group" with amino group coupled to any of the carbon atoms.

The "hydroxy $C_1$–$C_6$ alkyl" refers to the above-mentioned "$C_1$–$C_6$ alkyl" with any of the carbon atoms coupled to hydroxy group.

The "morpholino $C_1$–$C_6$ alkyl" refers to the above-mentioned "$C_1$–$C_6$ alkyl" with any of the carbon atoms coupled to morpholino group.

The "$C_1$–$C_6$ alkoxy" refers to a straight- or branched-chain alkoxy group such as methoxy, ethoxy, n-propoxy, isopropoxy, n-butoxy, tert-butoxy, n-pentyloxy, n-hexyloxy or the like.

The "halogen atom" may be fluorine, chlorine, bromine or iodine atom.

The compounds according to the present invention may be as follows, though the present invention is not limited to these compounds.

2-(benzimidazol-1-yl)-4,6-dimorpholino-1,3,5-triazine
2-(2-methylbenzimidazol-1-yl)-4,6-dimorpholino-1,3,5-triazine
2-(5,6-dimethylbenzimidazol-1-yl)-4,6-dimorpholino-1,3,5-triazine
4,6-dimorpholino-2-(2,5,6-trimethylbenzimidazol-1-yl)-1,3,5-triazine
2-(benzimidazol-1-yl)-4-(cis-2,6-dimethylmorpholino)-6-morpholino-1,3,5-triazine
4-(cis-2,6-dimethylmorpholino)-2-(2-methylbenzimidazol-1-yl)-6-morpholino-1,3,5-triazine
2-(benzimidazol-1-yl)-4-(trans-2,6-dimethylmorpholino)-6-morpholino-1,3,5-triazine
2-(benzimidazol-1-yl)-4-(cis-2,3-dimethylmorpholino)-6-morpholino-1,3,5-triazine 2-(benzimidazol-1-yl)-4-(trans-2,3-dimethylmorpholino)-6-morpholino-1,3,5-triazine
2-(benzimidazol-1-yl)-4-(2-methylmorpholino)-6-morpholino-1,3,5-triazine
2-(benzimidazol-1-yl)-4-(2,2-dimethylmorpholino)-6-morpholino-1,3,5-triazine
2-(benzimidazol-1-yl)-4-(2-ethylmorpholino)-6-morpholino-1,3,5-triazine
2-(benzimidazol-1-yl)-4-(2-chloromethylmorpholino)-6-morpholino-1,3,5-triazine
2-(benzimidazol-1-yl)-4-(2-fluoromethylmorpholino)-6-morpholino-1,3,5-triazine
2-(benzimidazol-1-yl)-4-(2-hydroxymethylmorpholino)-6-morpholino-1,3,5-triazine
2-(benzimidazol-1-yl)-4-morpholino-6-(2-trifluoromethylmorpholino)-1,3,5-triazine
2-(benzimidazol-1-yl)-4,6-bis(cis-2,6-dimethylmorpholino)-1,3,5-triazine
2-(benzimidazol-1-yl)-4-(cis-2,3-dimethylmorpholino)-6-(cis-2,6-dimethylmorpholino)-1,3,5-triazine
4,6-bis(cis-2,6-dimethylmorpholino)-2-(2,5,6-trimethylbenzimidazol-1-yl)-1,3,5-triazine
2-(benzimidazol-1-yl)-4-(trans-2,3-dimethylmorpholino)-6-(cis-2,6-dimethylmorpholino)-1,3,5-triazine
2-(benzimidazol-1-yl)-4-[2-(tert-butoxycarbonylaminomethyl)morpholino]-6-morpholino-1,3,5-triazine
2-(benzimidazol-1-yl)-4-[2-(N-benzyl-N-methylaminomethyl)morpholino]-6-morpholino-1,3,5-triazine
2-(2-aminomethylmorpholino)-4-(benzimidazol-1-yl)-6-morpholino-1,3,5-triazine
4-(cis-2,6-dimethylmorpholino)-2-(2-methylbenzimidazol-1-yl)-6-thiomorpholino-1,3,5-triazine
2-(benzimidazol-1-yl)-4-morpholino-6-piperidino-1,3,5-triazine
2-(benzimidazol-1-yl)-4-(4-hydroxypiperidino)-6-morpholino-1,3,5-triazine
2-(benzimidazol-1-yl)-4-morpholino-6-(4-oxopiperidino)-1,3,5-triazine
2-(benzimidazol-1-yl)-4-(3-hydroxypiperidino)-6-morpholino-1,3,5-triazine
2-(4-acetoxypiperidino)-4-(benzimidazol-1-yl)-6-morpholino-1,3,5-triazine
2-(benzimidazol-1-yl)-4-[3-(4-tert-butoxycarbonylaminobutyl)piperidino]-6-morpholino-1,3,5-triazine
2-(benzimidazol-1-yl)-4-morpholino-6-(piperazin-1-yl)-1,3,5-triazine
2-(benzimidazol-1-yl)-4-(4-methylpiperazin-1-yl)-6-morpholino-1,3,5-triazine
2-(benzimidazol-1-yl)-4-cyano-6-morpholino-1,3,5-triazine
2-(benzimidazol-1-yl)-4-dimethylamino-6-morpholino-1,3,5-triazine
2-(benzimidazol-1-yl)-4-[N-(2-hydroxyethyl)-N-methylamino]-6-morpholino-1,3,5-triazine
2-(benzimidazol-1-yl)-4-[N,N-di(2-hydroxyethyl)amino]-6-morpholino-1,3,5-triazine
2-(benzimidazol-1-yl)-4-(N-ethyl-N-2-morpholinoethyl)amino-6-morpholino-1,3,5-triazine
2-(benzimidazol-1-yl)-4-(N-butyl-N-2-morpholinoethyl)amino-6-morpholino-1,3,5-triazine
2-(benzimidazol-1-yl)-4-morpholino-6-thiomorpholino-1,3,5-triazine
2,4-di(benzimidazol-1-yl)-6-morpholino-1,3,5-triazine
2-(benzimidazol-1-yl)-4-(1,4-dioxa-8-azaspyro[4,5]dekan-8-yl)-6-morpholino-1,3,5-triazine
2-(benzimidazol-1-yl)-4,6-dimorpholinopyrimidine
4-(benzimidazol-1-yl)-2,6-dimorpholinopyrimidine
2-(2-methylbenzimidazol-1-yl)-4,6-dimorpholinopyrimidine
2-(5,6-dimethylbenzimidazol-1-yl)-4,6-dimorpholinopyrimidine
4,6-dimorpholino-2-(2,5,6-trimethylbenzimidazol-1-yl)-pyrimidine
2-(benzimidazol-1-yl)-4-(cis-2,6-dimethylmorpholino)-6-morpholinopyrimidine
2-(benzimidazol-1-yl)-4-(trans-2,6-dimethylmorpholino)-6-morpholinopyrimidine
2-(benzimidazol-1-yl)-4-(cis-2,3-dimethylmorpholino)-6-morpholinopyrimidine
4-(benzimidazol-1-yl)-2-(cis-2,3-dimethylmorpholino)-6-morpholinopyrimidine
4-(benzimidazol-1-yl)-6-(cis-2,3-dimethylmorpholino)-2-morpholinopyrimidine
2-(benzimidazol-1-yl)-4-(trans-2,3-dimethylmorpholino)-6-morpholinopyrimidine
4-(benzimidazol-1-yl)-2-(trans-2,3-dimethylmorpholino)-6-morpholinopyrimidine
4-(benzimidazol-1-yl)-6-(trans-2,3-dimethylmorpholino)-2-morpholinopyrimidine
2-(benzimidazol-1-yl)-4-(2,2-dimethylmorpholino)-6-morpholinopyrimidine
2-(benzimidazol-1-yl)-4-(2-ethylmorpholino)-6-morpholino-pyrimidine
2-(benzimidazol-1-yl)-4-(2-fluoromethylmorpholino)-6-morpholinopyrimidine
2-(benzimidazol-1-yl)-4-(2-hydroxymethylmorpholino)-6-morpholinopyrimidine
2-(benzimidazol-1-yl)-4-morpholino-6-(2-trifluoro-methylmorpholino)pyrimidine
2-(benzimidazol-1-yl)-4-(4-oxopiperidino)-6-morpholino-pyrimidine
2-(benzimidazol-1-yl)-4-(3-hydroxypiperidino)-6-morpholino-pyrimidine
2-(benzimidazol-1-yl)-4,6-bis(cis-2,6-dimethylmorpholino)pyrimidine
2-(benzimidazol-1-yl)-4-(cis-2,3-dimethylmorpholino)-6-(cis-2,6-dimethylmorpholino)pyrimidine
2-(benzimidazol-1-yl)-4-[2-(tert-butoxycarbonylaminomethyl)morpholino]-6-morpholinopyrimidine
2-(2-aminomethylmorpholino)-4-(benzimidazol-1-yl)-6-morpholinopyrimidine
4-(benzimidazol-1-yl)-2,6-bis(cis-2,6-dimethylmorpholino)pyrimidine
2-(benzimidazol-1-yl)-5-bromo-4-(cis-2,6-dimethylmorpholino)-6-morpholinopyrimidine
2-(benzimidazol-1-yl)-5-bromo-4-(trans-2,6-dimethylmorpholino)-6-morpholinopyrimidine
2-(benzimidazol-1-yl)-5-bromo-4,6-dimorpholinopyrimidine
4-(benzimidazol-1-yl)-5-bromo-2,6-dimorpholinopyrimidine
2-(benzimidazol-1-yl)-5-bromo-4-(trans-2,3-dimethylmorpholino)-6-morpholinopyrimidine
4-(benzimidazol-1-yl)-5-bromo-2-(trans-2,3-dimethylmorpholino)-6-morpholinopyrimidine
4-(benzimidazol-1-yl)-5-bromo-6-(trans-2,3-dimethylmorpholino)-2-morpholinopyrimidine
2-(benzimidazol-1-yl)-4-morpholino-6-piperidinopyrimidine
2-(4-acetoxypiperidino)-4-(benzimidazol-1-yl)-6-morpholinopyrimidine
2-(benzimidazol-1-yl)-4-morpholino-6-(piperazin-1-yl)-pyrimidine 2-(benzimidazol-1-yl)-4-(4-methylpiperazin-1-yl)-6-morpholinopyrimidine
2-(benzimidazol-1-yl)-4-cyano-6-morpholinopyrimidine
2-(benzimidazol-1-yl)-4-morpholino-6-thiomorpholinopyrimidine
2,4-di(benzimidazol-1-yl)-6-morpholinopyrimidine
4,6-di(benzimidazol-1-yl)-2-morpholinopyrimidine The compounds of the present invention may have asymmetric carbon atoms in its structure. It is to be understood that isomers due to such asymmetric carbon atom or combination (racemate) of any of the isomers are included in the category of the compounds according to the present invention.

Furthermore, the compounds of the present invention may be in the form of pharmaceutically acceptable acid addition salts. The appropriate salts which can be used include, for example, inorganic salts such as hydrochloride, sulfate, hydrobromide, nitrate and phosphate as well as organic acid salts such as acetate, oxalate, propionate, glycolate, lactate, pyruvate, malonate, succinate, maleate, fumarate, malate, tartarate, citrate, benzoate, cinnamate, methanesulfonate, benzenesulfonate, p-toluenesulfonate and salicylate.

Production Processes

The compounds of the present invention represented by the formula I may be prepared by, as shown in the following reaction formula, reacting cyanuric chloride or 2,4,6-trichloropyrimidine (compound II) as starting material with benzimidazole (compound V), morpholine (compound VI) and HR (compound VII) or sodium cyanate successively in the order named.

Reaction Formula

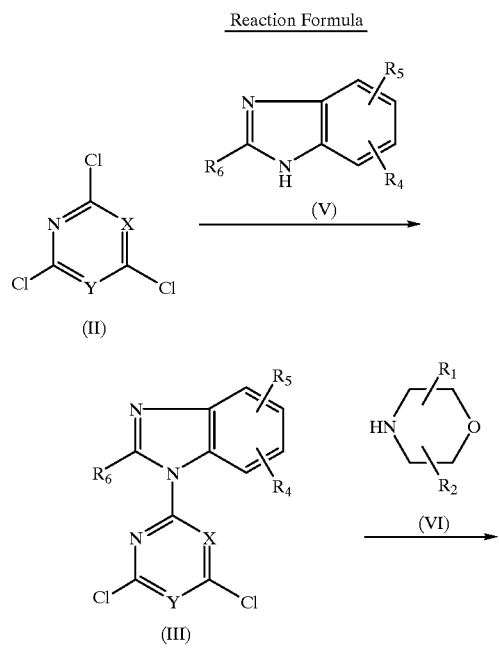

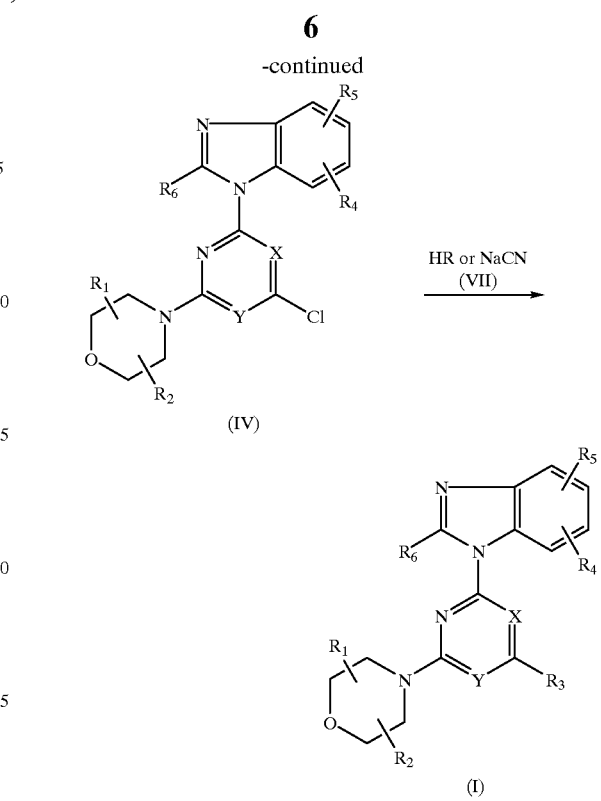

wherein $R_1$, $R_2$, $R_3$, $R_4$, $R_5$, $R_6$, X and Y are as defined above and R has the same definition of $R_3$ with the exception of cyano.

Next, the respective production processes will be described.

1) Production Process (i) of Intermediate III:

Reaction Formula (i)

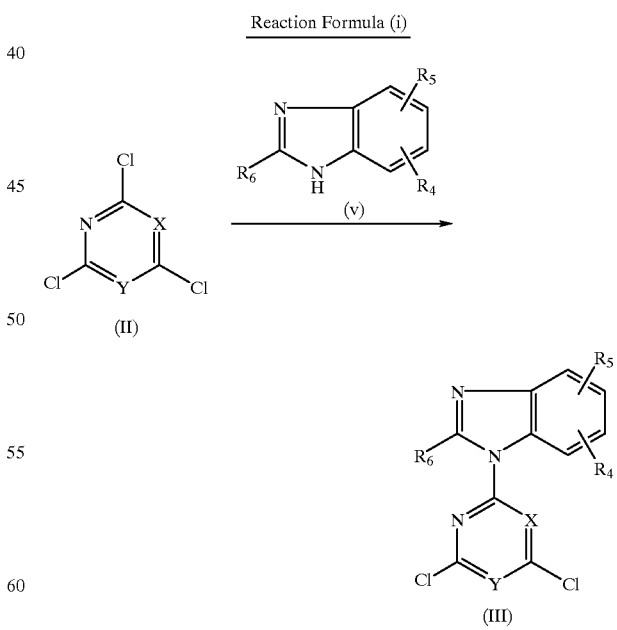

wherein $R_4$, $R_5$, $R_6$, X and Y are as defined above.

In a solvent and under the presence of hydrogen chloride trapping agents, cyanuric chloride or 2,4,6-trichloropyrimidine (compound II) is reacted with benzimidazole (compound V) to obtain the intermediate III.

The hydrogen chloride trapping agents used in this reaction may be, for example, sodium hydroxide, potassium hydroxide, sodium carbonate, potassium carbonate, triethylamine or pyridine. The solvent used may be acetone, toluene, xylene, dioxane, tetrahydrofuran or dichloroethane or N,N-dimethylformamide (DMF).

In this reaction, 0.5–1.2 mole of the compound V is used per mole of the compound II under the presence of 0.5–2 moles of the hydrogen chloride trapping agents. The reaction is made at the temperature of −15° C.–−5° C. for 0.5–2 hours, and further at the room temperature for 5–50 hours.

It is to be noted that benzimidazole (the compound V) may also be used as the hydrogen chloride trapping agent.

2) Production Process (ii) of Intermediate IV

Reaction Formula (ii)

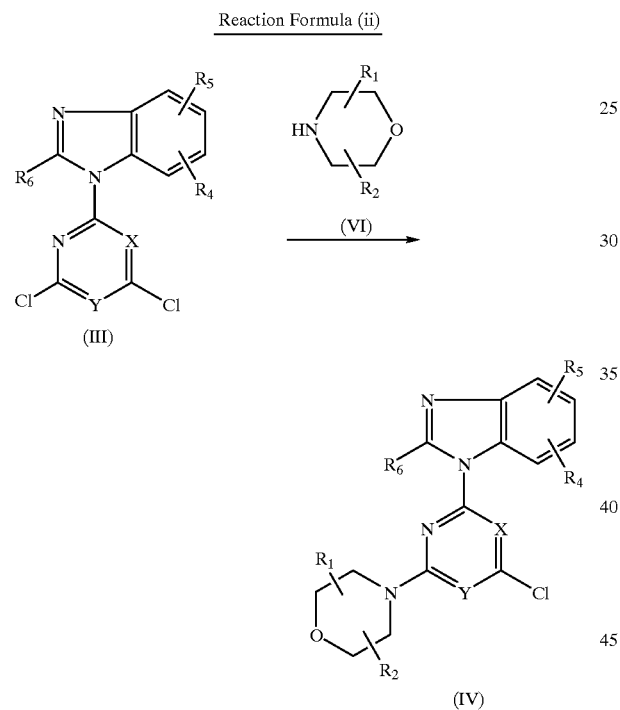

wherein $R_1$, $R_2$, $R_4$, R5, $R_6$, X and Y are as defined above.

In the solvent, the intermediate III obtained in the above-mentioned production process (i) is reacted with morpholine (compound VI) under the presence of hydrogen chloride trapping agents to obtain the intermediate IV.

The hydrogen chloride trapping agents used in this reaction may be the same as those in the above-mentioned production process (i). The solvent used may be DMF, acetone, toluene, xylene, dichloroethane or dichloromethane.

In this reaction, 0.5–1.2 mole of the compound VI is used per mole of the intermediate III and under the presence of 0.5–3 moles of the hydrogen chloride trapping agents. The reaction is made at the temperature of −5° C.–0° C. for 0.5–3 hours, and further at the room temperature for 5–50 hours.

It is to be noted that morpholine (the compound VI) may also be used as the hydrogen chloride trapping agents.

3) Production Process (iii) of the compound I

Reaction Formula (iii)

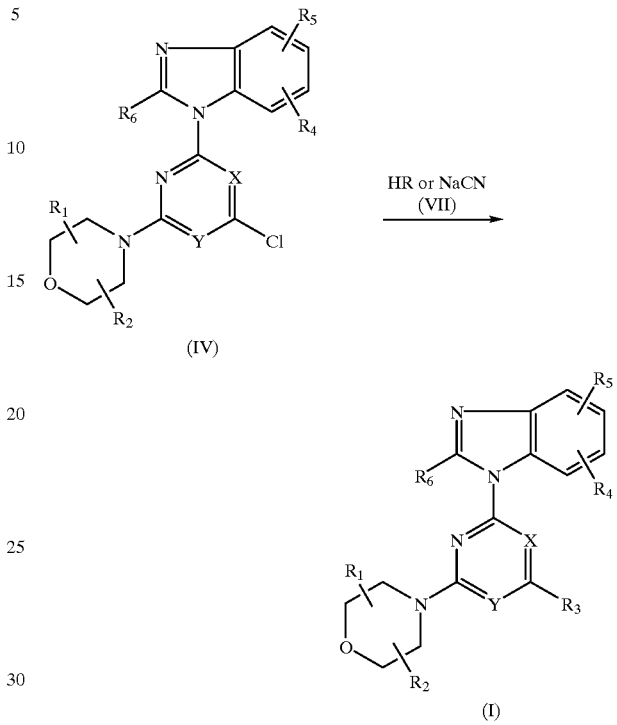

wherein R, $R_1$, $R_2$, $R_3$, $R_4$, $R_5$, $R_6$, X and Y are as defined above.

In the solvent, the intermediate IV obtained in the above-mentioned production process (ii) is reacted with sodium cyanate or reacted with HR (compound VII) under the presence of hydrogen chloride trapping agents to obtain the compound I according to the present invention.

The hydrogen chloride trapping agents used in this reaction may be the same as those in the above-mentioned production process (i). The solvent used may be DMF, dimethyl sulfoxide (DMSO), xylene or dichloroethane. In particular, DMSO is preferable in the case where sodium cyanate is to be reacted.

In this reaction, 1–5 moles of HR (the compound VII) or sodium cyanate is used per mole of the intermediate IV at the temperature between room temperature and 140° C. for 0.1–16 hours. In the case of the reaction under the presence of the hydrogen chloride trapping agents, 1–5 moles of the latter is used per mole of the intermediate IV.

In such production of the compound I and when the compounds VI and VII are the same, the production processes (ii) and (iii) may be carried out in a single step to obtain the compound I. In this case, the reaction conditions are as mentioned in the above with respect to the production process (ii) except that 2–2.2 moles of the compound VI or VII is used per mole of the compound III and that the reaction is made at the temperature of −10° C.–−5° C. for 0.1–5 hours, and further at room temperature for 3–50 hours.

In like manner, when the compounds V and VII are the same, the production processes (i) and (iii) may be carried out in a single step to obtain the corresponding intermediates. In this case, the reaction conditions are as mentioned in the above with respect to the production process (i) except that 2–4 moles of the compound V or VII is used per mole of the intermediate II and that the reaction is made at the temperature between room temperature and 120° C. for 0.1–50 hours.

The production processes (i), (ii) and (iii) may be carried out in any exchanged order. In such a case, the reaction conditions may be varied to an extent obvious to ordinary experts in the art.

The resultant products in the respective production processes may be separated and purified, as needs demand, by ordinary method such as extraction, condensation, neutralization, filtration, re-crystallization or column chromatography.

Acid-addition salts of the compounds I of the present invention may be prepared according to various methods well-known in the art. The appropriate acids used include, for example, inorganic acids such as hydrochloric, sulfuric, hydrobromic, nitric or phosphoric acid, and organic acids such as acetic, oxalic, propionic, glycolic, lactic, pyruvic, malonic, succinic, maleic, fumaric, malic, tartaric, citric, benzoic, cinnamic, methanesulfonic, benzenesulfonic, p-toluenesulfonic or salicylic acid.

Next, antitumor activities of the compounds I of the present invention will be described. Nos. of the tested compounds in the tests 1 and 2 correspond to those in Examples referred to hereinafter.

Controls used were the following s-triazine-series antitumor agents or medicines for estrogen-dependent diseases.

compound A: 2-(imidazol-1-yl)-4,6-dimorpholino-1,3,5-triazine (typical compound disclosed in the international publication WO93/17009)

compound B : hexamethylmelamine (HMM)

compound C : hydroxymethylpentamethylmelamine (HMPMM: metabolically active type of HMM)

Test 1

Used in the test were MCF-7 cells which were established from human breast cancer and were cultured routinely under the conditions of 37° C. and 5% $CO_2$, in RPMI 1640 medium supplemented with 10% fetal calf serum, HEPES buffer solution (25 mM) and kanamycin (0.1 mg/ml). Single cell suspension was prepared by adding trypsin/EDTA to the medium so as to be adjusted to $4.0 \times 10^4$ cells/ml. Test compounds were dissolved or suspended in DMSO or RPMI 1640 medium at a concentration of $1.0 \times 10^{-4}$–$1.0 \times 10^{-9}$ M.

The cell suspension and the sample solution or suspension were filled in a 96-wells microplate at a rate of 0.1 ml of the former and 0.1 ml of the latter per well and cultured at 37° C. for 72 hours in 5% $CO_2$.

50% Growth inhibition concentrations ($GI_{50}$ μM) were calculated from growth inhibitions at various sample concentrations. The results are as shown in Table 1.

TABLE 1

| test compound | $GI_{50}$ (μM) |
|---|---|
| compound 1 | 2.9 |
| compound 2 | 3.3 |
| compound 3 | 3.7 |
| compound 4 | 3.8 |
| compound 6 | 7.2 |
| compound 7 | 1.0 |
| compound 8 | 3.9 |
| compound 9 | 1.2 |
| compound 11 | 1.7 |
| compound 12 | 3.9 |
| compound 14 | 2.3 |
| compound 16 | 4.8 |
| compound 18 | 6.3 |
| compound 19 | 3.2 |

TABLE 1-continued

| test compound | $GI_{50}$ (μM) |
|---|---|
| compound 20 | 2.8 |
| compound 21 | 1.1 |
| compound 22 | 2.2 |
| compound 23 | 3.9 |
| compound 25 | 4.0 |
| compound 30 | 3.7 |
| compound 31 | 6.8 |
| compound 32 | 3.9 |
| compound 33 | 3.2 |
| compound 34 | 5.8 |
| compound 36 | 3.9 |
| compound 38 | 6.5 |
| compound 42 | 4.6 |
| compound 43 | 4.3 |
| compound 44 | 3.1 |
| compound 45 | 4.6 |
| compound 46 | 4.3 |
| compound 47 | 3.6 |
| compound 48 | 5.0 |
| compound 49 | 5.0 |
| compound 53 | 5.2 |
| compound A | 20 |
| compound B | >100 |
| compound C | >50 |

The above test results clearly revealed that the compounds of the present invention exhibit by far superior antitumor activities on human breast cancer cells than known controls A, B and C. Especially excellent antitumor activities were exhibited by the compounds I of the present invention wherein both $R_1$ and $R_2$ are methyl, $R_3$ being morpholino, all of $R_4$, $R_5$ and $R_6$ being hydrogen atom.

The compounds of the present invention were also effective in vitro tests using human non small cell lung cancer cells and human colonic cancer cells and therefore positively expected is application of the compounds according to the present invention on treatment of various human solid cancers.

Test 2

The treated group to which the test sample was administered consisted of seven mice while the control group consisted of ten mice. Six weeks old male mice ($BDF_1$, 25±2.5 g) were employed as host animals.

M5076 mouse reticulum cell sarcoma cells routinely cultured in abdominal of C57BL/6 male mice were diluted with cold Hanks solution and $1.0 \times 10^6$ cells of them were transplanted subcutaneously into left breast of each mouse. The samples prepared by suspending test compounds in 1% hydroxypropyl cellulose (HPC) were abdominally administered for 9 days after the day after the transplantation. After 21 days passed from the transplantation of the tumor, the mice were killed and the tumors were extracted out to measure the tumor weights of the respective groups.

Effect of sample was calculated as tumor growth inhibition by the following formula:

$$\text{Tumor Growth Inhibition } (\%) = (1 - T/C) \times 100$$

T: tumor weight of group with sample administered
C: tumor weight of control group The results are as shown in Table 2.

TABLE 2

| test compound | administered amount (mg/kg) | Growth Inhibition (%) |
|---|---|---|
| compound 1 | 200 | 94.7 |
| compound 9 | 200 | 98.6 |
| compound 11 | 200 | 88.3 |
| compound 19 | 200 | 98.1 |
| compound 22 | 100 | 83.8 |
| compound A | 70 | 5.0 |
| compound B | 100 | 38.8 |

The above test results revealed that the compounds of the present invention also exhibit remarkable cancer cell growth inhibition effect in vivo tests and that they apparently exhibit excellent effects even in comparison with growth inhibition of the controls A and B administered in appropriate amounts.

Moreover, it was found out that the compounds of the present invention exhibit remarkable cancer cell growth inhibition effect even in the case where the samples were orally administered in the above test.

Test 3

The acute toxicity was determined by orally or abdominally administrating the compound 9 or 22 of the present invention, which was adjusted by distilled water added with 1% of hydroxypropyl cellulose, to $BDF_1$ male mice (6-weeks-old, having a body weight of 25±2.5 g) and $LD_{50}$ was obtained over observation for 14 days. As a result, it was found out that $LD_{50}$ of any of the compounds was 400–800 mg/kg.

The compounds of the present invention may be administered orally or parenterally to mammals and especially to humans. In oral administration, the compounds may be in the appearance of tablets, coated tablets, powders, granules, capsules, microcapsules, syrups and the like; and in parenteral administration, in the appearance of injections which may include soluble freeze-drying appearance, suppositories and the like. In the preparation of these appearances, pharmaceutically acceptable excipient, binders, lubricants, disintegrators, suspensions, emulsifiers, antiseptics, stabilizers and dispersing agents, for example, lactose, sucrose, starch, dextrin, crystalline cellulose, kaolin, calcium carbonate, talc, magnesium stearate, distilled water and physiological saline solution may be used.

The dosage for humans may depend on the condition of the disease to be treated, the age and weight of the patient and the like. A daily dosage for an adult may be in the range of from 200 to 2,000 mg and may be given in divided doses 2 or 3 times a day.

BEST MODE FOR CARRYING OUT THE INVENTION

Next, the present invention is more specifically illustrated with reference to the following Examples. It is to be, however, noted that the present invention is not limited to these Examples.

EXAMPLE 1

2-(benzimidazol-1-yl)-4-(cis-2,6-dimethyl-morpholino)-6-morpholino-1,3,5-triazine (compound 1)

(1) Cyanuric chloride (10.0 g, 54 mmol) dissolved in acetone (100 ml) was cooled to −5° C., slowly added with triethylamine (4.7 ml, 49 mmol) dropwise and further, slowly added with morpholine (7.5 g, 54 mmol) dropwise. The reaction mixture was stirred at the same temperature for one hour and then stirred at room temperature for one hour. The reaction solution was poured into water (500 ml). The precipitated crystals were collected by filtration, washed with trace amount of acetone and dried to obtain 9.7 g (yield: 69%) of 2,4-dichloro-6-morpholino-1,3,5-triazine as colorless crystals with melting point of 155° C.–157° C.

(2) The obtained 2,4-dichloro-6-morpholino-1,3,5-triazine (6.0 g, 25mmol) dissolved in DMF (100 ml) was cooled to −5° C., added with anhydrous pottasium carbonate (5 g, 36 mmol) and benzimidazole (3.0 g, 35 mmol), stirred for 30 minutes and further stirred at room temperature for 15 hours. The reaction mixture was added with water (500 ml). The precipitated crystals were collected by filtration, washed with trace amount of acetone and dried to obtain 5.2 g (yield: 64%) of 2-(benzimidazol-1-yl)-4-chloro-6-morpholino-1,3,5-triazine with melting point of 201° C.–203° C. as colorless crystals.

(3) The obtained 2-(benzimidazol-1-yl)-4-chloro-6-morpholino-1,3,5-triazine (320 mg, 1.0 mmol) dissolved in DMF (20 ml) was added with potassium carbonate (430 mg, 3.2 mmol) and cis-2,6-dimethylmorpholine (140 mg, 1.2 mmol) and stirred at room temperature for 45 minutes. The reaction mixture was condensed under reduced pressure and the obtained residue was added with dichloromethane and water and shaken for mixing. The separated organic layer was washed with water and dried over anhydrous magnesium sulfate. The solvent was removed under reduced pressure and the residue was purified by silica gel column chromatography to obtain 360 mg (yield: 90%) of the titled compound as colorless crystals.
Melting Point: 195–197° C.
NMR(CDCl$_3$) δ: 1.30(6H, m), 2.5–2.8(2H, m), 3.6–3.8 (2H, m), 3.8–4.0(8H, m), 4.5–4.7(2H, m), 7.3–7.5(2H, m), 7.83(1H, d, J=9 Hz), 8.36(1H, d, J=9 Hz), 8.97(1H, s)
MS m/z: 395(M$^+$)

In accordance with the procedure of Example 1, the following compounds were obtained from corresponding starting materials.

2-(benzimidazol-1-yl)-4,6-dimorpholino-1,3,5-triazine (compound 2)
Appearance: colorless crystals
Melting Point: 222–224° C.
NMR(CDCl$_3$) δ: 3.8–4.0(16H, m), 7.3–7.5(2H, m), 7.8–7.9(1H, m), 8.3–8.4(1H, m), 8.97(1H, s)
MS m/z: 367(M$^+$)

2-(2-methylbenzimidazol-1-yl)-4,6-dimorpholino-1,3,5-triazine (compound 3)
Appearance: colorless crystals
Melting Point: 218–220° C.
NMR(CDCl$_3$) δ: 2.95(3H, s), 3.7–3.8(8H, m), 3.7–3.9 (8H, m), 7.2–7.3(2H, m), 7.6–7.7(1H, m), 8.1–8.2(1H, m)
MS m/z: 381(M$^+$)

2-(benzimidazol-1-yl)-4-cyano-6-morpholino-1,3,5-triazine (compound 4)
Appearance: colorless crystals
Melting Point: 271–273° C.
NMR(CDCl$_3$) δ: 3.7–4.1(8H, m), 7.3–7.5(2H, m), 7.83 (1H, d, J=8 Hz), 8.37(1H, d, J=8 Hz), 8.95(1H, s)
MS m/z: 307(M$^+$)

2-(benzimidazol-1-yl)-4-(4-hydroxypiperidino)-6-morpholino-1,3,5-triazine (compound 5)
Appearance: colorless crystals
Melting Point: 201–203° C.
NMR(CDCl$_3$) δ: 1.5–1.7(2H, m), 1.9–2.1(2H, m), 3.4–3.6 (2H, m), 3.8–4.1(9H, m), 4.3–4.5(2H, m), 7.3–7.5(2H, m), 7.81(1H, d, J=9 Hz), 8.39(1H, d, J=9 Hz), 8.99(1H, s)

MS m/z: 381(M⁺)

2-(benzimidazol-1-yl)-4-morpholino-6-(2-trifluoromethylmorpholino)-1,3,5-triazine (compound 6)
Appearance: colorless crystals
Melting Point: 140–142° C.
NMR(CDCl₃) δ: 3.1–3.3(2H, m), 3.6–4.0(10H, m), 4.1–4.3(1H, m), 4.5–4.7(1H, m), 4.7–4.9(1H, m), 7.3–7.5 (2H, m), 7.89(1H, d, J=6 Hz), 8.38(1H, d, J=8 Hz), 9.14(1H, brs)
MS m/z: 435(M⁺)

2-(benzimidazol-1-yl)-4-(cis-2,3-dimethylmorpholino)-6-morpholino-1,3,5-triazine (compound 7)
Appearance: colorless crystals
Melting Point: 172–174° C.
NMR(CDCl₃) δ: 1.35(3H, d, J=7 Hz), 1.40(3H, d, J=7 Hz), 3.36(1H, dt, J=5 Hz, 13 Hz), 3.7–4.0(11H, m), 4.4–4.7 (2H, m), 7.3–7.5(2H, m), 7.82(1H, dd, J=2 Hz, 6 Hz), 8.37(1H, dd, J=2 Hz, 6 Hz), 8.98(1H, s)
MS m/z: 395(M⁺)

2-(benzimidazol-1-yl)-4-(cis-2,3-dimethylmorpholino)-6-(cis-2,6-dimethylmorpholino)-1,3,5-triazine (compound 8)
Appearance: colorless crystals
Melting Point: 204–206° C.
NMR(CDCl₃) δ: 1.2–1.5(12H, m), 2.5–2.8(2H, m), 3.36 (1H, dt, J=4 Hz, 13 Hz), 3.6–4.0(5H, m), 4.4–4.8(4H, m), 7.3–7.5(2H, m), 7.82(1H, dd, J=2 Hz, 6 Hz), 8.37(1H, dd, J=2 Hz, 6 Hz), 8.98(1H, s)
MS m/z: 423(M⁺)

2-(benzimidazol-1-yl)-4-(trans-2,3-dimethylmorpholino)-6-morpholino-1,3,5-triazine (compound 9)
Appearance: colorless crystals
Melting Point: 166–168° C.
NMR(CDCl₃) δ: 1.2–1.4(6H, m), 2.6–2.8(2H, m), 3.6–4.0 (10H, m), 4.5–4.7(2H, m), 7.3–7.5(2H, m), 7.82(1H, dd, J=2 Hz, 6 Hz), 8.37(1H, dd, J=2 Hz, 6 Hz), 8.97(1H, d, J=2 Hz)
MS m/z: 395(M⁺)

2-(benzimidazol-1-yl)-4-(trans-2,3-dimethylmorpholino)-6-(cis-2,6-dimethylmorpholino)-1,3,5-triazine (compound 10)
Appearance: colorless crystals
Melting Point: 189–191° C.
NMR(CDCl₃) δ: 1.2–1.4(12H, m), 2.5–2.8(2H, m), 3.1–3.4(1H, m), 3.5–3.8(4H, m), 3.9–4.1(1H, m), 4.3–5.8 (4H, m), 7.3–7.5(2H, m), 7.82(1H, dd, J=2 Hz, 6 Hz), 8.37(1H, dd, J=2 Hz, 6 Hz), 8.98(1H, d, J=2 Hz)
MS m/z: 423(M⁺)

2-(benzimidazol-1-yl)-4-(2,2-dimethylmorpholino)-6-morpholino-1,3,5-triazine (compound 11)
Appearance: colorless crystals
Melting Point: 172–173° C.
NMR(CDCl₃) δ: 1.28(6H, s), 3.4–4.0(14H, m), 7.3–7.5 (2H, m), 7.82(1H, dd, J=2 Hz, 6 Hz), 8.3–8.5(1H, m), 8.97(1H, s)
MS m/z: 395(M⁺)

2-(benzimidazol-1-yl)-4-(2-ethylmorpholino)-6-morpholino-1,3,5-triazine (compound 12)
Appearance: colorless crystals
Melting Point: 140–142° C.
NMR(CDCl₃) δ: 1.05(3H, t, J=7 Hz), 1.5–1.7(2H, m), 2.7–2.9(1H, m), 3.0–3.3(1H, m), 3.3–3.5(1H, m), 3.5–4.1 (10H, m), 4.5–4.8(2H, m), 7.3–7.5(2H, m), 7.82(1H, dd, J=2 Hz, 6 Hz), 8.38(1H, dd, J=2 Hz, 6 Hz), 8.97(1H, s)
MS m/z: 395(M⁺)

2-(benzimidazol-1-yl)-4-(2-chloromethylmorpholino)-6-morpholino-1,3,5-triazine (compound 13)
Appearance: colorless crystals
Melting Point: 181–183° C.
NMR(CDCl₃) δ: 2.9–3.1(1H, m), 3.1–3.3(1H, m), 3.6–4.2 (13H, m), 4.5–4.9(2H, m), 7.3–7.5(2H, m), 7.83(1H, d, J=6 Hz), 8.38(1H, d, J=7 Hz), 8.97(1H, s)
MS m/z: 415(M⁺)

2-(benzimidazol-1-yl)-4-(trans-2,6-dimethylmorpholino)-6-morpholino-1,3,5-triazine (compound 14)
Appearance: colorless crystals
Melting Point: 210–212° C.
NMR(CDCl₃) δ: 1.2–1.3(6H, m), 3.4–3.5(1H, m), 3.7–4.1 (12H, m), 4.1–4.2(1H, m), 7.3–7.4(2H, m), 7.8–7.9(1H, m), 8.3–8.4(1H, m), 8.97(1H, s)
MS m/z: 395(M⁺)

2-(benzimidazol-1-yl)-4-morpholino-6-piperidino-1,3,5-triazine (compound 15)
Appearance: colorless crystals
Melting Point: 160–162° C.
NMR(CDCl₃) δ: 1.5–1.8(6H, m), 3.7–4.0(12H, m), 7.3–7.5(2H, m), 7.81(1H, d, J=9 Hz), 8.39(1H, d, J=9 Hz), 8.99(1H, s)
MS m/z: 365(M⁺)

2-(benzimidazol-1-yl)-4-(2-methylmorpholino)-6-morpholino-1,3,5-triazine (compound 16)
Appearance: colorless crystals
Melting Point: 159–161° C.
NMR(CDCl₃) δ: 1.30(3H, d, J=6 Hz), 2.7–2.9(1H, m), 3.0–3.3(1H, m), 3.5–4.1(11H, m), 4.5–4.7(2H, m), 7.3–7.5 (2H, m), 7.82(1H, d, J=6 Hz), 8.38(1H, d, J=8 Hz), 9.14(1H, s)
MS m/z: 381(M⁺)

2-(benzimidazol-1-yl)-4-morpholino-6-(piperazin-1-yl)-1,3,5-triazine (compound 17)
Appearance: colorless crystals
Melting Point: 202–205° C.
NMR(CDCl₃) δ: 2.96(4H, m), 3.7–4.0(12H, m), 7.3–7.5 (2H, m), 7.81(1H, d, J=9 Hz), 8.38(1H, d, J=9 Hz), 8.98(1H, s)
MS m/z: 366(M⁺)

2-(benzimidazol-1-yl)-4-[2-(tert-butoxycarbonylaminomethyl)morpholino]-6-morpholino-1,3,5-triazine (compound 18)
Appearance: colorless crystals
Melting Point: 155–158° C.
NMR(CDCl₃) δ: 1.46(9H, s), 2.8–3.0(1H, m), 3.1–3.3 (2H, m), 3.4–3.7(2H, m), 3.7–4.0(10H, m), 4.5–4.7(2H, m), 4.8–5.0(1H, brs), 7.3–7.5(2H, m), 7.89(1H, d, J=7 Hz), 8.39(1H, d, J=7 Hz), 9.14(1H, s)
MS m/z: 496(M⁺)

2-(5,6-dimethylbenzimidazol-1-yl)-4,6-dimorpholino-1,3,5-triazine (compound 30)
Appearance: colorless crystals
Melting Point: 200–202° C.
NMR(CDCl₃) δ: 2.38(3H, s), 2.40(3H, s), 3.8–4.1(16H, m), 7.56(1H, s), 8.14(1H, s), 8.85(1H, s)
MS m/z: 395(M⁺)

2-(benzimidazol-1-yl)-4-[2-(N-benzyl-N-methylaminomethyl)morpholino]-6-morpholino-1,3,5-triazine (compound 31)
Appearance: colorless crystals
Melting Point: 112–118° C.
NMR(CDCl₃) δ: 2.2–2.4(3H, brs), 2.5–4.8(19H, m), 7.2–7.4(7H, m), 7.8–7.9(1H, m), 8.3–8.5(1H, brs), 8.98(1H, s)
MS m/z: 500(M⁺)

2-(benzimidazol-1-yl)-4-(2-fluoromethylmorpholino)-6-morpholino-1,3,5-triazine (compound 32)
Appearance: colorless crystals Melting Point: 194–196° C.
NMR(CDCl$_3$) δ: 2.9–3.3(2H, m), 3.6–4.0(9H, m), 4.0–4.2 (1H, m), 4.4–4.8(5H, m), 7.3–7.5(2H, m), 7.83(1H, d, J=7 Hz), 8.36(1H, d, J=7 Hz), 8.97(1H, s)
MS m/z: 399(M$^+$)

4-(cis-2,6-dimethylmorpholino)-2-(2-methylbenzimidazol-1-yl)-6-morpholino-1,3,5-triazine (compound 33)
Appearance: colorless crystals
Melting Point: 173–175° C.
NMR(CDCl$_3$) δ: 1.28(6H, d, J=16 Hz), 2.6–2.8(2H, m), 2.98(3H, s), 3.5–4.0(10H, m), 4.5–4.7(2H, m), 7.2–7.4(2H, m), 7.6–7.8(1H, m), 8.1–8.3(1H, m)
MS m/z: 409(M$^+$)

2-(benzimidazol-1-yl)-4-(2-hydroxymethylmorpholino)-6-morpholino-1,3,5-triazine (compound 34)
Appearance: colorless crystals
Melting Point: 207–209° C.
NMR(CDCl$_3$) δ: 2.1–2.2(1H, m), 2.9–3.3(2H, m), 3.7–4.2 (13H, m), 4.5–4.8(2H, m), 7.3–7.5(2H, m), 7.81(1H, d, J=9 Hz), 8.37(1H, d, J=9 Hz), 9.00(1H, s)
MS m/z: 397(M$^+$)

4,6-bis(cis-2,6-dimethylmorpholino)-2-(2,5,6-trimethylbenzimidazol-1-yl)-1,3,5-triazine (compound 35)
Appearance: colorless crystals
Melting Point: 203–205° C.
NMR(CDCl$_3$) δ: 1.29(12H, d, J=6 Hz), 2.37(6H, s), 2.5–2.8(4H, m), 2.92(3H, s), 3.6–3.8(4H, m), 4.5–4.7(4H, m), 7.43(1H, s)., 8.03(1H, s)
MS m/z: 465(M$^+$)

2-(benzimidazol-1-yl)-4-(3-hydroxypiperidino)-6-morpholino-1,3,5-triazine (compound 36)
Appearance: colorless crystals
Melting Point: 225–226° C.
NMR(CDCl$_3$) δ: 1.5–1.8(2H, m), 1.8–2.1(2H, m), 2.20 (1H, d, J=4 Hz), 3.5–4.2(12H, m), 4.2–4.4(1H, m), 7.3–7.5 (2H, m), 7.80(1H, d, J=9 Hz), 8.37(1H, d, J=9 Hz), 8.96(1H, s) MS m/z: 381(M$^+$)

2-(benzimidazol-1-yl)-4-morpholino-6-(4-oxopiperidino)-1,3,5-triazine (compound 37)
Appearance: colorless crystals
Melting Point: 220–222° C.
NMR(CDCl$_3$) δ: 2.58(4H, t, J=6 Hz), 3.8–3.9(4H, m), 3.9–4.0(4H, m), 4.1–4.3(4H, m), 7.3–7.5(2H, m), 7.83(1H, d, J=9 Hz), 8.38(1H, d, J=9 Hz), 8.99(1H, s)
MS m/z: 379(M$^+$)

2-(4-acetoxypiperidino)-4-(benzimidazol-1-yl)-6-morpholino-1,3,5-triazine (compound 38)
Appearance: colorless crystals
Melting Point: 153–155° C.
NMR(CDCl$_3$) δ: 1.7–1.9(2H, m), 1.9–2.1(2H, m), 2.10 (3H, s), 3.6–4.0(10H, m), 4.1–4.4(2H, m), 5.0–5.2(1H, m), 7.3–7.5(2H, m), 7.82(1H, d, J=9 Hz), 8.38(1H, d, J=9 Hz), 8.98(1H, s)
MS m/z: 423(M$^+$)

2-(benzimidazol-1-yl)-4-(4-methylpiperazin-1-yl)-6-morpholino-1,3,5-triazine (compound 39)
Appearance: colorless crystals
Melting Point: 210–212° C.
NMR(CDCl$_3$) δ: 2.37(3H, s), 2.4–2.6(4H, m), 3.7–4.1 (12H, m), 7.3–7.5(2H, m), 7.83(1H, d, J=9 Hz), 8.38(1H, d, J=9 Hz), 8.98(1H, s)
MS m/z: 380(M$^+$)

2-(benzimidazol-1-yl)-4-dimethylamino-6-morpholino-1,3,5-triazine (compound 40)
Appearance: colorless crystals
Melting Point: 135–137° C.
NMR(CDCl$_3$) δ: 3.20(3H, s), 3.29(3H, s), 3.7–4.0(8H, m), 7.3–7.5(2H, m), 7.82(1H, d, J=9 Hz), 8.44(1H, d, J=9 Hz), 9.00(1H, s)
MS m/z: 325(M$^+$)

2-(benzimidazol-1-yl)-4-[N-(2-hydroxyethyl)-N-methylamino]-6-morpholino-1,3,5-triazine (compound 41)
Appearance: colorless crystals
Melting Point: 162–165° C.
NMR(CDCl$_3$) δ: 3.2–3.4(3H, m), 3.7–4.0(12H, m), 7.3–7.5(2H, m), 7.7–7.9(1H, m), 8.3–8.5(1H, m), 8.96(1H, s)
MS m/z: 355(M$^+$)

2-(benzimidazol-1-yl)-4-[N,N-di(2-hydroxyethyl)amino]-6-morpholino-1,3,5-triazine (compound 42)
Appearance: colorless crystals
Melting Point: 220–222° C.
NMR(CDCl$_3$) δ: 3.7–4.0(16H, m), 7.3–7.5(2H, m), 7.7–7.9(1H, m), 8.3–8.4(1H, m), 8.93(1H, s)
MS m/z: 385(M$^+$)

2-(benzimidazol-1-yl)-4-[1,4-dioxa-8-azaspiro[4,5]decan-8-yl)-6-morpholino-1,3,5-triazine (compound 48)
Appearance: colorless crystals
Melting Point: 214–216° C.
NMR(CDCl$_3$) δ: 1.7–1.9(4H, m), 3.7–4.1(16H, m), 7.2–7.4(2H, m), 7.7–7.9(1H, m), 8.3–8.5(1H,m), 8.98(1H, s)
MS m/z: 423(M$^+$)

2-(benzimidazol-1-yl)-4-(N-ethyl-N-2-morpholinoethyl) amino-6-morpholino-1,3,5-triazine (compound 49)
Appearance: colorless crystals
Melting Point: 158–162° C.
NMR(CDCl$_3$) δ: 1.2–1.4(3H, m), 2.5–2.7(7H, m), 3.6–3.9 (15H, m), 7.3–7.4(2H, m), 7.8–7.9(1H, m), 8.4–8.5(1H, m), 8.9–9.0(1H, m)
MS m/z: 438(M$^+$)

2-(benzimidazol-1-yl)-4-[3-(4-tert-butoxycarbonylaminobutyl)piperidino]-6-morpholino-1,3,5-triazine (compound 50)
Appearance: colorless crystals
Melting Point: 143–145° C.
NMR(CDCl$_3$) δ: 1.2–2.0(22H, m), 2.6–2.9(1H, m), 2.9–3.2(2H, m), 3.7–4.0(8H, m), 4.4–4.8(2H, m), 7.3–7.5 (2H, m), 7.8–7.9(1H, m), 8.3–8.5(1H, m), 8.98(1H, s)
MS m/z: 536(M$^+$)

4-(cis-2,6-dimethylmorpholino)-2-(2-methylbenzimidazol-1-yl)-6-thiomorpholino-1,3,5-triazine (compound 51)
Appearance: colorless crystals
Melting Point: 213–215° C.
NMR(CDCl$_3$) δ: 1.25(6H, d, J=6 Hz), 2.7–2.8(6H, m), 2.94(3H, s), 3.5–3.8(2H , m), 4.1–4.3(4H, m), 4.5–4.7(2H, m), 7.2–7.4(2H, m), 7.6–7.8(1H, m), 8.1–8.2(1H, m)
MS m/z: 425(M$^+$)

EXAMPLE 2

2-(benzimidazol-1-yl)-4-(cis-2,6-dimethyl-morpholino)-6-morpholinopyrimidine (compound 19)

(1) 30.5 g (167 mmol) of 2,4,6-trichloropyrimidine dissolved in DMF (300 ml) was cooled to −5° C., added with potassium carbonate (40 g) and benzimidazole (17.7 g, 150 mmol) and stirred for 30 minutes. The reaction mixture was further stirred at room temperature overnight. The reaction mixture was added with water (500 ml) and the precipitated crystals were collection by filtration. The obtained crude crystals were purified by silica gel chromatography to obtain 12.8 g (yield: 32%) of 2-(benzimidazol-1-yl)-4,6-dichloropyrimidine with melting point of 173° C. –175° C. as colorless crystals.

(2) The obtained 2-(benzimidazol-1-yl)-4,6-dichloropyrimidine (2.08 g, 7.85 mmol) dissolved in DMF(30 ml) was cooled to –5° C., added with anhydrous potassium carbonate (3.0 g, 22 mmol) and morpholine (0.68 g. 7.85 mmol) and stirred for 30 minutes. The reaction mixture was further stirred at room temperature overnight and condensed under reduced pressure. The residue was added with methylene chloride and water and shaken for mixing. The organic layer was separated out and washed with water, dried over anhydrous magnesium sulfate and condensed. The obtained residue was purified by silica gel column chromatography to obtain 1.90 g (yield 77%) of 2-(benzimidazol-1-yl)-4-chloro-6-morpholinopyrimidine with melting point of 178° C.–181° C.

(3) To the obtained 2-(benzimidazol-1-yl)-4-chloro-6-morpholinopyrimidine (318 mg, 1.00 mmol) dissolved in dioxane—water solution (4:1), sodium hydroxide (100 mg, 4.3 mmol) and cis-2,6-dimethylmorpholine (126 mg, 1.20 mmol) were added and stirred at 80° C. for 12 hours. The reaction mixture was condensed under reduced pressure and the obtained residue was mixed with methylene chloride and water and shaken. Organic layer was separated from the mixture and washed with water and dried over anhydrous magnesium sulfate. The solvent was removed out under reduced pressure and the residue was purified by silica gel column chromatography to obtain 340 mg of the titled compound (yield: 86%).

Appearance: colorless crystals
Melting Point: 196–197° C.
NMR(CDCl$_3$) δ: 1.30(6H, d, J=6 Hz), 2.65(2H, t, J=12 Hz), 3.6–3.8(6H, m), 3.85(4H, t, J=10 Hz), 4.15(2H, d, J=12 Hz), 5.45(1H, s), 7.2–7.4(2H, m), 7.82(1H, dd, J=2 Hz, 6 Hz), 8.37(1H, dd, J=2 Hz, 6 Hz), 8.95(1H, s)
MS m/z: 394(M$^+$)

In accordance with the procedure of the Example 2, the following compounds were obtained from the corresponding starting materials.

2-(benzimidazol-1-yl)-4-(trans-2,6-dimethylmorpholino)-6-morpholinopyrimidine (compound 20)
Appearance: colorless crystals
Melting Point: 185–187° C.
NMR(CDCl$_3$) δ: 1.29(6H, d, J=7 Hz), 3.3–3.5(2H, m), 3.6–3.9(10H, m), 4.1–4.2(2H, m), 5.43(1H, m), 7.3–7.5(2H, m), 7.82(1H, d, J=6 Hz), 8.38(1H, d, J=6 Hz), 8.96(1H, m)
MS m/z: 394(M$^+$)

2-(benzimidazol-1-yl)-4-(cis-2,3-dimethylmorpholino)-6-morpholinopyrimidine (compound 21)
Appearance: colorless crystals
Melting Point: 163–165° C.
NMR(CDCl$_3$) δ: 1.37(3H, d, J=7 Hz), 1.39(3H, d, J=7 Hz), 3.3–3.5(1H, m), 3.6–4.2(13H, m), 5.44(1H, s), 7.2–7.4 (2H, m), 7.82(1H, d, J=9 Hz), 8.38(1H, d, J=9 Hz), 8.96(1H, s)
MS m/z: 394(M$^+$)

2-(benzimidazol-1-yl)-4-(trans-2,3-dimethylmorpholino)-6-morpholinopyrimidine (compound 22)
Appearance: colorless crystals
Melting Point: 179–181° C.
NMR(CDCl$_3$) δ: 1.20(3H, d. J=7 Hz), 1.24(3H, d, J=7 Hz), 3.1–3.3(1H, m), 3.6–4.3(13H, m), 5.44(1H, s), 7.2–7.4 (2H, m), 7.82(1H, d, J=9 Hz), 8.38(1H, d, J=9 Hz), 8.96(1H, s)
MS m/z: 394(M$^+$)

2-(benzimidazol-1-yl)-4-morpholino-6-thiomorpholino-pyrimidine (compound 23)

Appearance: colorless crystals
Melting Point: 242–244° C.
NMR(CDCl$_3$) δ: 2.71(4H, brs), 3.80(4H, brs), 3.8–4.0 (4H, m), 4.1–4.3(4H, m), 5.45(1H, s), 7.3–7.5(2H, m), 7.82(1H, dd, J=2 Hz, 7 Hz), 8.38(1H, dd, J=2 Hz, 7 Hz), 8.97(1H, m)
MS m/z: 382(M$^+$)

2-(benzimidazol-1-yl)-4-morpholino-6-(piperazin-1-yl) pyrimidine (compound 24)
Appearance: colorless crystals
Melting Point: 190–193° C.
NMR(CDCl$_3$) δ: 3.01(4H, t, J=5 Hz), 3.6–3.8(8H, m), 3.85(4H, t, J=5 Hz), 5.48(1H, s), 7.3–7.5(2H, m), 7.81(1H, d, J=9 Hz), 8.40(1H, d, J=9 Hz), 8.97(1H, s)
MS m/z: 365(M$^+$)

2-(benzimidazol-1-yl)-4-[2-(tert-butoxycarbonylamino-methyl)morpholino]-6-morpholinopyrimidine (compound 25)
Appearance: colorless crystals
Melting Point: 183–185° C.
NMR(CDCl$_3$) δ: 1.47(9H, s), 2.8–3.0(1H, m), 3.0–3.2 (1H, m), 3.2–3.3(1H, m), 3.4–3.6(1H, m), 3.6–3.8(5H, m), 3.8–3.9(4H, m), 4.0–4.2(2H, m), 4.2–4.4(2H, m), 4.9–5.0 (1H, br), 5.48(1H, s), 7.3–7.5(2H, m), 7.83(1H, d, J=8 Hz), 8.36(1H, d, J=8 Hz), 8.95(1H, s)
MS m/z: 495(M$^+$)

2-(benzimidazol-1-yl)-4,6-dimorpholinopyrimidine (compound 43)
Appearance: colorless crystals
Melting Point: 247–249° C.
NMR(DMSO-d$_6$) δ: 3.6–3.8(16H, m), 5.90(1H, s), 7.29 (1H, t, J=8 Hz), 7.37(1H, t, J=8 Hz), 7.72(1H, d, J=8 Hz), 8.37(1H, d, J=8 Hz), 9.08(1H, s)
MS m/z: 366(M$^+$)

2,4-di(benzimidazol-1-yl)-6-morpholinopyrimidine (compound 44)
Appearance: colorless crystals
Melting Point: 276–278° C.
NMR(DMSO-d$_6$) δ: 3.7–4.0(8H, m), 7.14(1H, s), 7.3–7.5 (4H, m), 7.7–7.9(2H, m), 8.35(1H, d, J=8 Hz), 8.45(1H, d, J=8 Hz), 9.16(1H, s), 9.21(1H, s)
MS m/z: 397(M$^+$)

4-(benzimidazol-1-yl)-2,6-dimorpholinopyrimidine (compound 45)
Appearance: colorless crystals
Melting Point: 231–233° C.
NMR(DMSO-d$_6$) δ: 3.6–3.8(16H, m), 6.55(1H, s), 7.2–7.5(2H, m), 7.74(1H, d, J=7 Hz), 8.29(1H, d, J=7 Hz), 9.01(1H, s)
MS m/z: 366(M$^+$)

4,6-di(benzimidazol-1-yl)-2-morpholinopyrimidine (compound 46)
Appearance colorless crystals
Melting Point: 301–303° C.
NMR(DMSO-d$_6$) δ: 3.8–4.0(8H, m), 7.41(2H, t, J=7 Hz), 7.46(2H, t, J=7 Hz), 7.65(1H, s), 7.80(2H, d, J=7 Hz), 8.43(2H, d, J=7 Hz), 9.21(2H, s)
MS m/z: 397(M$^+$)

2-(benzimidazol-1-yl)-5-bromo-4,6-dimorpholinopyrimidine (compound 47)
Appearance: colorless crystals
Melting Point: 181–185° C.
NMR(CDCl$_3$) δ: 3.6–3.7(8H, m), 3.8–3.9(8H, m), 7.2–7.4 (2H, m), 7.8–7.9(1H, m), 8.3–8.4(1H, m), 8.92(1H, s)
MS m/z: 446(M$^+$)

EXAMPLE 3

Hydrochloride of 2-(2-aminomethylmorpholino)-4-(benzimidazol-1-yl)-6-morpholino-1,3,5-triazine (compound 26)

125 mg (0.315 mmol) of 2-(benzimidazol-1-yl)-4-[2-(tert-butoxycarbonylaminomethyl)morpholino]-6- morpholino-1,3,5-triazine (compound 18) was stirred in 2 ml of 4 N dioxane chloride solution at room temperature for 1 hour. The solvent was removed and 5 ml of ether was added. The precipitated crystals were filtered out and washed with 10 ml of ether to obtain 95 mg of the titled compound (yield: 90%).

Appearance: colorless crystals
Melting Point: >250° C.
NMR(D$_2$O) δ: 2.9–3.2(3H, m), 3.4–3.8(11H, m), 3.8–4.0 (1H, m), 4.1–4.4(2H, m), 7.2–7.4(2H, m), 7.36(1H, d, J=7 Hz), 7.98(1H, d, J=8 Hz), 9.09(1H, s)
MS m/z: 397[M+1]$^+$ In accordance with the procedure of the Example 3, the following compounds were obtained from the corresponding starting materials.

hydrochloride of 2-(benzimidazol-1-yl)-4-morpholino-6-(1-piperazinyl)-1,3,5-triazine (compound 27)
Appearance: colorless crystals
Melting Point: 260–265° C.
NMR(D$_2$O) δ: 3.3–3.5(4H, m), 3.7–4.0(8H, m), 4.0–4.2 (4H, m), 7.4–7.7(2H, m), 7.7–7.9(1H, m), 8.0–8.2(1H, m), 9.4–9.6(1H, br)
MS m/z: 367[M+1]$^+$ hydrochloride of 2-(2-aminomethylmorpholino)-4-(benzimidazol-1-yl)-6-morpholinopyrimidine (compound 28)
Appearance: colorless crystals
Melting Point: 94–96° C.
NMR(D$_2$O) δ: 2.6–2.8(1H, m), 2.9–3.2(3H, m), 3.3–3.8 (9H, m), 3.8–4.2(4H, m), 5.40(1H, s), 7.3–7.5(2H, m), 7.61(1H, d, J=8 Hz), 8.0–8.1(1H, br), 9.44(1H, s)
MS m/z: 396[M+1]$^+$ hydrochloride of 2-(benzimidazol-1-yl)-4-morpholino-6-(1-piperadinyl)-pyrimidine (compound 29)
Appearance: colorless crystals
Melting Point: 266–270° C.
NMR(D$_2$O) δ: 3.4–3.5(4H, m), 3.5–3.7(4H, m), 3.8–4.0 (8H, m), 5.56(1H, s), 7.5–7.7(2H, m), 7.78(1H, d, J=8 Hz), 8.17(1H, d, J=8 Hz), 9.65(1H, s)
MS m/z: 366[M+1]$^+$ hydrochloride of 2-(benzimidazol-1-yl)-4-(N-ethyl-N-2-morpholinoethyl)amino-6-morpholino-1,3,5-triazine (compound 52)
Appearance: colorless crystals
Melting Point: >250° C.
NMR(D$_2$O) δ: 1.1–1.3(3H, m), 3.2–4.1(20H, m), 4.7–4.8 (2H, m), 7.4–7.6(2H, m), 7.6–7.8(1H, m), 8.2–8.4(1H, m), 9.3–9.5(1H, m)
MS m/z: 439[M+1]$^+$ hydrochloride of 2-[3-(4-aminobutyl)piperidino]-4-(benzimidazol-1-yl)-6-morpholino-1,3,5-triazine (compound 53)
Appearance: colorless crystals
Melting point: >250° C.
NMR(D$_2$O) δ: 1.2–2.0(12H, m), 2.6–3.2(3H, m), 3.7–4.0 (8H, m), 4.5–4.8(2H, m), 7.3–7.5(2H, m), 7.8–7.9(1H, m), 8.3–8.5(1H, m), 8.98(1H, s)
Ms m/z: 437[M+1]$^+$ Capability of Exploitation in Industry The compounds of the present invention exhibit apparently by far strong antitumor activity with no aromatase inhibitory activity in comparison with conventional s-triazine and pyrimidine derivatives and can be applied to treatment on solid cancers.

What is claimed is:

1. A heterocyclic compound in which s-triazine or pyrimidine is substituted with benzimidazole and morpholine and which is represented by the formula I or a pharmaceutically acceptable acid addition salt thereof:

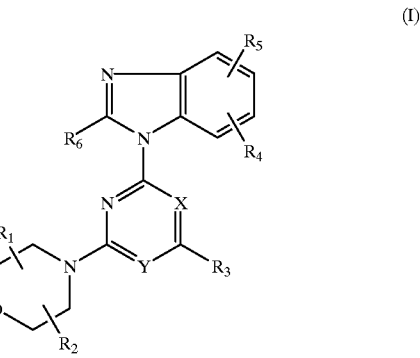

(I)

wherein X and Y represent a nitrogen atom, or one of X or Y represents a nitrogen atom and the other represents CR$_7$, wherein R$_7$ represents hydrogen or a halogen atom;

R$_1$, R$_2$, R$_4$, R$_5$ and R$_6$ each represent a hydrogen atom or a C$_1$–C$_6$ alkyl group; R$_3$ represents
morpholino optionally substituted with one or two C$_1$–C$_6$ alkyl groups, trifluoromethyl, hydroxymethyl, monohalogenomethyl or CH$_2$NR$_8$R$_9$, wherein R$_8$ represents a hydrogen atom or C$_1$–C$_6$ alkyl, and R$_9$ represents a hydrogen atom, C$_1$–C$_6$ alkoxycarbonyl or benzyl; piperidino optionally substituted with hydroxy, acetoxy, oxo, 4,4-ethlenedioxy or amino C$_1$–C$_6$ alkyl; piperazinyl optionally substituted with C$_1$–C$_6$ alkyl; thiomorpholino; benzimidazolyl; cyano; or
NR$_{10}$R$_{11}$ wherein R$_{10}$ and R$_{11}$ represent a hydrogen atom, C$_1$–C$_6$ alkyl, hydroxy C$_1$–C$_6$ alkyl or morpholino C$_1$–C$_6$ alkyl.

2. The compound according to claim 1 wherein one of X and Y is nitrogen atom.

3. The compound according to claim 1 wherein one of X and Y is nitrogen atom and both R$_1$ and R$_2$ are methyl.

4. The compound according to claim 1 wherein one of X and Y is nitrogen atom; both R$_1$ and R$_2$ are methyl and R$_3$ is morpholino.

5. The compound according to claim 1 wherein one of X and Y is nitrogen atom; both R$_1$ and R$_2$ are methyl; R$_3$ is morpholino and all of R$_4$, R$_5$ and R$_6$ are hydrogen atom.

6. The compound according to claim 1 wherein both of X and Y are nitrogen atom.

7. The compound according to claim 1 wherein both X and Y are nitrogen atom and both R$_1$ and R$_2$ are methyl.

8. The compound according to claim 1 wherein both of X and Y are nitrogen atom; both R$_1$ and R$_2$ are methyl and R$_3$ is morpholino.

9. The compound according to claim 1 wherein both X and Y are nitrogen atom; both R$_1$ and R$_2$ are methyl; R$_3$ is morpholino and all of R$_4$, R$_5$ and R$_6$ are hydrogen atom.

10. A pharmaceutical composition comprising the compound of claim 1, or a pharmaceutically acceptable acid addition salt thereof, and a pharmaceutically acceptable diluent or carrier.

11. A method of treating human lung cancer, comprising administering to a patient in need of such treatment an effective amount of the compound of claim 1 or a pharmaceutically acceptable addition salt thereof.

12. A method of treating human breast cancer, comprising administering to a patient in need of such treatment an effective amount of the compound of claim 1 or a pharmaceutically acceptable addition salt thereof.

13. A method of treating human colon cancer, comprising administering to a patient in need of such treatment an effective amount of the compound of claim 1 or a pharmaceutically acceptable addition salt thereof.

* * * * *